United States Patent [19]

Dunn

[11] 4,375,468

[45] Mar. 1, 1983

[54] CONSTANT ORDER RELEASE ASPIRIN COMPOSITION AND METHOD OF TREATING ARTHRITIS

[75] Inventor: James M. Dunn, Englewood, Colo.

[73] Assignee: Verex Laboratories, Inc., Englewood, Colo.

[21] Appl. No.: 366,594

[22] Filed: Apr. 8, 1982

Related U.S. Application Data

[63] Continuation of Ser. No. 282,544, Jul. 13, 1981, abandoned.

[51] Int. Cl.$^3$ .......................... A61K 9/30; A61K 9/56; A61K 31/60
[52] U.S. Cl. ....................................... 424/230; 424/39
[58] Field of Search .................................. 424/39, 230

[56] References Cited

U.S. PATENT DOCUMENTS

3,384,546  5/1965  Palermo ............................. 424/230
3,627,583  4/1969  Troy ................................... 424/230
4,079,132  3/1978  Lin ..................................... 424/230

Primary Examiner—Stanley J. Friedman
Attorney, Agent, or Firm—Joyce R. Niblack

[57] ABSTRACT

A constant order release aspirin tablet comprising aspirin, from 0.5 to 10 weight percent of a hydrogenated vegetable oil and from 0.5 to 7 weight percent of a saccharide selected from the group consisting of lactose, sucrose, dextrose fructose and maltose. The aspirin tablet is administered once or twice a day for the chronic treatment of arthritis, and has substantially lessened gastrointestinal side effects.

13 Claims, No Drawings

CONSTANT ORDER RELEASE ASPIRIN COMPOSITION AND METHOD OF TREATING ARTHRITIS

This is a continuation, of application Ser. No. 06/282,544, filed July 13, 1981 now abandoned.

BACKGROUND OF THE INVENTION

The number of people who have arthritis is increasing. It is currently estimated that between 35–40 million people in the United States alone, or one out of every seven individuals, has arthritic symptoms which require medical treatment. There will be one person every thirty three seconds who will develop symptomatic arthritis and need medical treatment.

Despite the introduction of newer, non-steroidal drugs designed to treat the arthritic patient, aspirin remains the drug of choice. Aspirin has both anti-inflammatory and pain relieving benefits. In the reference pharmacology textbook, Goodman and Gilman, The Pharmacological Basis of Therapeutics, 6th Edition, Section V, Chapter 28, the entire section on analgesic; anti-inflammatory drugs is characterized as follows: "The anti-inflammatory, analgesic and antipyretic drugs are a heterogenous group of compounds often chemically unrelated which nevertheless share certain therapuetic actions and side effects. The prototype for these compounds is aspirin."

One problem with aspirin, as usually formulated for typical, commercial formulations is that it has to be administered four to six times a day to produce satisfactory pain relief and suppression of inflammation. When drugs or medications have to be administered more than twice daily, patient compliance is approximately forty five (45%) percent. When the therapeutic agent is given once or twice daily, compliance by the patient increases to about seventy five (75%) percent. Further, standard aspirin formulations can produce a high incidence, seventy (70) percent, of gastrointestinal side effects including nausea, heartburn, vomiting, gastric erosion, gastroduodenal ulcers as well as bleeding from the gastrointestinal tract. Approximately twenty-five (25) percent of patients taking regular aspirin tablets complain of ringing in the ears and other central nervous system side effects.

Because of the side effects of this valuable, therapeutic agent, there has been a long standing need for an aspirin product which can be taken once or twice daily and which provides a slow, steady release of aspirin to decrease side effects without loss of efficacy. The present invention provides one such product.

PRIOR ART

There is a substantial body of prior art on timed-release pharmaceutical preparations and processes for preparing such formulations, and timed-release pharmaceutical preparations have become well-accepted over the past several decades. The National Formulary recognizes "Timed-Release Tablets and Capsules" and describes such dosage forms as follows:

"As understood herein, timed-release would include those tablets and capsules variously known as 'delayed action,' 'extended-release,' 'prolonged action' or 'repeat action,' but would not include tablets specifically identified as 'enteric coated'." [N.F. XIII, 882(1970)].

The prior art also refers to such preparations as "sustained" or "controlled" release.

A number of U.S. and foreign patents have issued in this field. Generally, the timed-release preparations of the prior art comprise coatings with waxes, fats, derivatives of waxes and fats and various cellulosic and synthetic polymers. Other timed or sustained-release preparations comprise an insoluble matrix having the active medicament enclosed or esconsed therein. Representative patents include U.S. Pat. Nos. 2,921,883 and 2,665,236.

There exists a body of prior art directed specifically to timed or sustained or controlled release aspirin preparations and a variety of such formulations have been described.

One approach to the problem has included attempts to develop a sustained or controlled release of aspirin, in a tablet formulation using microencapsulated aspirin granules. See for example, U.S. Pat. Nos. 3,488,418, 3,341,416 and 3,155,590.

Another approach has been the use of aspirin in a dispersed, water-soluble colloid which is then coated with a rupturable but non-digestible material which is permeable to water. See U.S. Pat. No. 3,247,066.

U.S. Pat. No. 3,115,411 discloses an aspirin encapsulation method wherein particles of aspirin are first given a quick, thin coating of a film-forming material, a non-toxic, hydrophobic material, and are then coated with successive coatings of an organic solvent resistant material.

Press, U.S. Pat. No. 2,953,497 teaches a procedure for the preparation of timed-release granules comprising mixing aspirin, corn starch and sucrose to form a formulation and then coating the formed particles with shellac or cellulose acetate phthalate.

Guy et al. U.S. Pat. No. 3,906,086 teaches an improvement in the process of preparing a sustained release aspirin product employing cellulose acetate phthalate as the coating material. Guy et al. incorporate a plasticizing agent in the coating solution and compress the plasticized, cellulose acetate phthalate-coated aspirin particles without the use of a tabletting excipient such as corn starch.

Kornblum U.S. Pat. Nos. 3,632,739 and 4,012,498 broadly disclose the concept of coating granules with a solution of sustained release material and compressing the coated granules into tablets. Eberhardt U.S. Pat. No. 3,362,881 describes a similar system. However, the direct result is an aspirin tablet that is an impractical size.

The use of fats and waxes with and without associated use of cellulose ethers or esters has been broadly disclosed. See for example Robinson, U.S. Pat. No. 2,805,977 and Playfair U.S. Pat. No. 3,147,187, and Berger U.S. Pat. No. 3,344,029.

While various attempts have been made to reduce the side effects of aspirin by either enteric coating, or timed or sustained or controlled release formulations, the prior art did not provide a satisfactory solution to the problem.

Dunn and Lampard U.S. Ser. No. 194,453, filed Oct. 17, 1980, a continuation-in-part of U.S. Ser. No. 111,430, filed Jan. 11, 1980, assigned to Boots Pharmaceuticals, Inc., Shreveport, La., discloses controlled release aspirin formulations comprising aspirin, a release controlling agent selected from the group consisting of cellulose acetate phthalate, cellulose acetate derivatives, shellac, zein, acrylic resins, ethyl-cellulose, hydroxyproprylmethylcellulose phthalate, sandarac and modified shellac and an erosion promoting agent selected from the group consisting of corn starch, rice starch, potato and other vegetable starches, modified starch, starch derivatives, cellulose, cellulose derivatives.

SUMMARY OF THE INVENTION

The present invention provides a constant order release aspirin tablet which has lessened side effects over conventional aspirin formulations, and is an improvement over my constant order release aspirin formulation of copending U.S. Ser. No. 194,453, filed Oct. 17, 1980. The aspirin tablet of the present invention comprises from 650 to 800 mg of aspirin, from 0.5 to 10 weight percent, preferably from 1 to 6 weight percent, of an edible, hydrophobic hydrogenated, solid vegetable oil and from 0.5 to 7 weight percent of a saccharide, preferably from 0.5 to 4.5 weight percent. The aspirin tablet of the present invention may additionally comprise from 0.15 to 1.5 weight percent, preferably from 0.3 to 0.78 weight percent of a cellulose ether or ester and/or a lubricant such as talc.

The term "constant order release aspirin tablet" refers to an aspirin tablet wherein the in vitro release of aspirin from the tablet, using a USP dissolution apparatus, pH 7.5, is constant and linear against time until all the aspirin is released. When plotted on an x,y graph using the formula $$k = dc/dt$$

wherein k=constant, dc=decreasing concentration and dt=decreasing time, a straight line is formed. Calculation of the data points by linear regression analysis gives an r value of 0.85-1.0 An r value of 1.0 is a perfect straight line.

DETAILED DESCRIPTION OF THE PREFERRED EMBODIMENTS

The constant order release aspirin tablet of the present invention comprises an intimate, compressed admixture of aspirin, a granulating agent selected from the group consisting of an edible, hydrophobic vegetable oil alone or in combination with minor amounts of a cellulose ester or ether, and a tabletting excipient selected from the group consisting of lactose, sucrose, dextrose, fructose and maltose.

The preferred granulating agent used in the practice of this invention is a powdered, hydrogenated cottonseed oil sold under the trademark LUBRITAB® Brussels Nomenclature 15.12 by Edward Mendell Co., Inc., Carmel, N.Y. 10512. Hydrophobic, hydrogenated vegetable oils useful in the practice of this invention include, but are not limited to coconut oil, safflower oil, sunflower oil, and the like.

Lactose is the preferred tabletting excipient.

The preferred cellulose ether employed in this invention is hydroxymethylpropyl cellulose. Other suitable cellulose ethers include, but are not limited to, ethylcellulose, hydroxyethyl cellulose, etc.

The preferred cellulose ester is cellulose acetate phthalate. Other suitable esters include cellulose acetate, cellulose acid phthalate, cellulose nitrate, etc.

While cellulose ethers or esters may be employed in minor amounts in the formulations of the present invention to improve the granulation properties, their use is optional.

The preferred solvents are denatured alcohol and methylene chloride as a mixture [1:1(v/v)]. Other suitable solvents include but are not limited to lower-aliphatic alcohols such as methanol, iso-propanol, n-propanol, etc., acetone and lower aliphatic ketones such as methyl ethyl ketone, chloroform, carbon tetrachloride, ethyl acetate, and non-chlorinated hydrocarbons.

Generally speaking, the constant order release aspirin tablets of the present invention are prepared by dissolving the hydrophobic, hydrogenated oil in a suitable solvent, and carefully admixing the solution with a dry blended powder of aspirin and a tabletting excipient such as lactose to form a wet granulation. This granulation is dried and then screened through a 14-20 mesh/inch screen. The sized granules may then be compressed in a rotary or single station punch press. If a lubricant is required, talc may be added to the formed granules prior to tabletting.

Because the tablet is produced with a smooth, waxy surface, the tablets will accept printing directly on their surface without additional preparation. Tablet identification may also be made by debossing the finished product during compression.

The addition of cellulose ethers and/or esters to the solvent before or after the dispersion of the hydrogenated oil or wax may be used to increase the viscosity and hardness of the granulating fluid and prolong the release rate of the drug without significantly affecting the size of the finished tablet.

Additionally, a suitable granulation may be formed by dry blending the hydrogenated oil or wax, aspirin and tabletting excipient and adding an appropriate quantity of solvent with or without the addition of the cellulose ether and/or esters. The granulation thus formed is dried and then passed through a 14-20 mesh screen, blended with talc and compressed on a rotary or single tablet punch press.

Aspirin tablets made in this manner do not have the proclivity for gastro-intestinal irritation which is a failure of regular soluble aspirin. They perform in a constant order release manner in vitro as discussed above. In humans, blood levels of active drug can be measured for up to 12 hours following a single dose, and surprisingly, pain relief is noted within 30 minutes as opposed to 2 hours or more with my prior formulations, and have lessened lower gastrointestinal side effects.

Because of the unique and superior constant order release properties, aspirin tablets made by the above process and from the above ingredients can be administered twice a day to provide 24 hour suppression of pain and inflammation.

Turning to the preferred process of the present invention, the preferred hydrophobic material, hydrogenated cottonseed oil, a digestible vegetable oil, is dissolved and dispersed in a solvent which is used to make a wet granulation. The amount of material used is small, ranging from 0.5-10 weight percent of the final tablet weight, preferably 1-6 weight percent.

A minor amount of cellulose ether or ester, i.e. 0.15-1.5 weight percent of the finished tablet, preferably from 0.3 to 0.78 weight percent, can be suspended in the solvent. The cellulose ethers and esters improve the viscosity of the solvent mixture and further serve to retard the release of the aspirin from the tablet matrix. These compounds used by themselves in this formulation would be ineffective in providing significant retardation of drug release. When these agents are used in combination with the preferred hydrogenated vegetable oil, cottonseed oil, a synergistic phenomena is noted.

It is critical that the wet granulation be dried completely before screening. Failure to observe this technique will result in rupture of the granules and a loss of the constant order release profile of the tablet. In conventional, prior art tabletting procedures, the wet granulations are generally screened immediately after formation and then dried. However, if the prior art processes are employed, the constant order release profile of the aspirin tablets of the present invention will be destroyed. The process of this invention provides a further unexpected advantage in that it eliminates the necessity for employing a hot melt or spraying technique generally required when dealing with waxes or oils.

The following examples further illustrate the present invention.

EXAMPLE 1

Aspirin tablets containing 650 mg of aspirin per tablet were prepared from the following formulation and by the following process.

| Ingredient | Amount |
| --- | --- |
| Aspirin (80 mesh) | 650 gm |
| Hydrogenated Cotton Seed Oil | 30 gm |
| Lactose | 15 gm |
| Hydroxypropylmethyl cellulose (Mehtocel-E50) | 4 gm |
| Ethanol (denatured) | 40 ml |
| Methylene Chloride | 40 ml |
| Talc, USP | 3 gm |

The aspirin, cottonseed oil and lactose were deaggregated and placed in a Hobart mixer. The hydroxypropryl methyl cellulose was added slowly to the solvents while being mixed with a high speed stirrer. After the cellulose ether was completely dissolved, it was added to the aspirin mixture over a 30 second period with constant stirring. Further high speed stirring was carried out until a wet granular mass was formed. The material was discharged onto trays and completely dried. The granular material was then screened dry through a No. 16 mesh screen. The material was then blended with talc and compressed on a rotary press using half inch flat, beveled tooling to produce aspirin tablets containing 650 mg of aspirin each and having a tablet hardness of 8-10 Kp (Schleuniger).

EXAMPLE 2

Aspirin tablets containing 650 mg of aspirin each were prepared from the following formulation.

| Ingredient | Amount |
| --- | --- |
| Aspirin, 80 mesh | 650 gm |
| Lactose | 15 gm |
| Hydrogenated cottonseed oil | 30 gm |
| Denatured ethanol | 40 ml |
| Methylene Chloride | 40 ml |
| Talc | 3 gm |

The aspirin and lactose were deaggregated into the bowl of a Hobart mixer and dry blended. The hydrogenated cottonseed oil was dissolved with high-speed stirring in the ethanol-methylene chloride solution. This solution was added to the aspirin-lactose mixture for 30 seconds with constant stirring. High speed mixing was continued until a granulation formed. The granulation was discharged on to stainless steel trays and dried. After complete drying, the material was screened through a number 18 mesh screen, blended without a lubricant, and tabletted on a rotary press. A tablet with a smooth, shiny surface and having a hardness of 8-10 Kp (Schleuniger) was produced.

EXAMPLE 3

Aspirin tablets containing 650 mg per tablet were formulated from the following composition.

| Ingredient | Amount |
| --- | --- |
| Aspirin | 650 gm |
| Lactose | 15 gm |
| Hydrogenated cottonseed oil | 30 gm |
| Hydroxypropylmethylcellulose (E-50) | 3 gm |
| Cellulose acetate phthalate | 1 gm |
| Denatured ethanol | 40 ml |
| Methylene Chloride | 40 ml |
| Talc | 3 gm |

The presence of a small amount of hydroxypropylmethyl cellulose and cellulose acetate phthalate gives a more prolonged constant order release.

The aspirin, lactose and powdered cottonseed oil were deaggregated and placed in the bowl of a Hobart mixer. The cellulose products were dissolved in the solvent by high speed stirring. After dry-blending the aspirin-lactose-powdered cottonseed oil mixture, was granulated by pouring the solvent and cellulose products mixture over the powder in a period of 30 seconds. Continuous mixing was carried out until a wet granular mass was formed. This was then discharged on to stainless steel trays and dried. When drying was completed, the granules were screened through a #16 mesh screen and blended with talc. The material was then tableted without difficulty into aspirin tablets having a hardness of 8-12 Kp (Schleuniger).

EXAMPLE 4

Aspirin tablets containing 650 mg/tablet of aspirin were formulated from the following composition.

| Ingredient | Amount |
| --- | --- |
| Aspirin (80 mesh) | 650 gm |
| Lactose | 15 gm |
| Hydrogenated cottonseed oil | 30 gm |
| Denatured Ethanol | 50 ml |
| Methylene Chloride | 50 ml |
| Talc | 3 gm |

The powdered cottonseed oil and lactose were deaggregated into the bowl of a Hobart mixer and dry blended for 5 minutes. The solvents were then added to produce an over-wetted granulation which is placed on stainless steel trays and dried. After drying, the granules were passed through a #16 mesh screen, blended with talc and compressed in a rotary tablet press. The tablets had a tablet hardness of 8-10 Kp (Schleuniger).

EXAMPLE 5

To demonstrate the retardent effects of the cellulose product on tablet erosion, tablets of Examples 2 and 3 were subjected to a disintegration test as described in U.S.P. XX, page 958. The results are set forth in Table 1.

TABLE 1

| % Tablet Residue After 4 Hours, pH 7.5, 37° C. | | | | | |
|---|---|---|---|---|---|
| Tablets Made Example 2 | | | Tablets Made Example 3 | | |
| Start Weight mg | 4 hours Weight mg | Percent Residue | Start Weight mg | 4 hours Weight mg | Percent Residue |
| 707.2 | 12.4 | 1.8% | 687.5 | 151.9 | 22.1% |
| 695.8 | 12.6 | 1.8% | 688.4 | 129.5 | 18.8% |
| 707.2 | 15.9 | 2.2% | 685.2 | 152.1 | 22.2% |
| 700.7 | 17.1 | 2.4% | 687.1 | 138.5 | 20.2% |
| 706.9 | 10.2 | 1.4% | 686.5 | 153.8 | 22.4% |
| 709.3 | 13.7 | 1.9% | 675.8 | 133.1 | 19.7% |
| 704.5 mg | 13.7 mg | 1.9% | 685.1 | 143.2 | 20.9% |

EXAMPLE 6

While the tablets prepared in the manner described exhibited a steady constant erosion, to be considered a constant order release drug requires testing by dissolution. In this procedure, six randomly selected tablets made by the method of Example 1 were placed in an approved U.S.P. dissolution apparatus and assayed for aspirin according to the method described in U.S.P. XX 56, 959–960. The amount of acetylsalicylic acid found was 666 mg per tablet which was 102.5% of the theoretical amount. The average tablet weight was 705.4 mg determined by randomly weighing 20 tablets. The dissolution data is set forth in table 2.

TABLE 2

| | | DISSOLUTION | | | |
|---|---|---|---|---|---|
| Tablet No. | Tablet Weight (mg) | 1 Hour | 2 Hour | 3 Hour | 4 Hour |
| 1 | 692.7 | 108 | 160 | 205 | 260 |
| 2 | 691.9 | 115 | 189 | 301 | 390 |
| 3 | 709.5 | 149 | 230 | 403 | 526 |
| 4 | 723.6 | 137 | 210 | 349 | 450 |
| 5 | 685.3 | 155 | 225 | 443 | 588 |
| 6 | 689.7 | 203 | 300 | 482 | 616 |
| mean wt. (mg) | 698.8 mg | 144.5 | 219.0 | 363.8 | 471.7 |
| % of theoretical amount available (650 mg) | | 22.24% | 33.69% | 55.97% | 72.57% | linear regression analysis of mean mg weight or percent drug released over time: r = 0.993

EXAMPLE 7

A single dose bioavailability study was performed in two healthy male volunteers. After a complete medical evaluation, the two subjects were given 1300 mg (2–650 mg tablets) of aspirin as a single dose formulate as described in Example 1. The subjects ingested the aspirin tablets with 250 ml of water. Blood samples were obtained and analyzed by high pressure liquid chromatography for both acetylsalicylic acid and salicylic acid. The results of this analysis at the specified time intervals are shown below in Tables 3 and 4 respectively.

TABLE 3

| | Acetylsalicylic Acid mcg/ml | | | | | | | | | | |
|---|---|---|---|---|---|---|---|---|---|---|---|
| Subject | 0.5 Hr | 1 Hr. | 2 Hr. | 3 Hr. | 4 Hr. | 5 Hr. | 6 Hr. | 7 Hr. | 8 Hr. | 10 Hr | 12 Hr. |
| #1 | 0.45 | 0.50 | 0.59 | 0.50 | 0.53 | 0.48 | 0.55 | 0.51 | 0.46 | 0.50 | 0.32 |
| #2 | 0.31 | 0.34 | 0.41 | 0.60 | 0.50 | 0.47 | 0.50 | 0.36 | 0.20 | N.D. | N.D. |
| mean | 0.38 | 0.42 | 0.50 | 0.55 | 0.52 | 0.47 | 0.53 | 0.44 | 0.33 | 0.25 | 0.16 |

TABLE 4

| | Salicylic Acid mcg/ml | | | | | | | | | | |
|---|---|---|---|---|---|---|---|---|---|---|---|
| Subject | 0.5 Hr | 1 Hr. | 2 Hr. | 3 Hr. | 4 Hr. | 5 Hr. | 6 Hr. | 7 Hr. | 8 Hr. | 10 Hr | 12 Hr. |
| #1 | 1.8 | 3.2 | 5.7 | 7.6 | 9.1 | 9.4 | 14.7 | 12.3 | 14.6 | 15.9 | 13.6 |
| #2 | 1.1 | 1.8 | 4.1 | 3.4 | 4.5 | 5.3 | 4.7 | 4.8 | 5.4 | 8.7 | 8.1 |
| mean | 1.5 | 2.5 | 4.9 | 5.5 | 6.8 | 7.4 | 9.7 | 8.6 | 10.0 | 12.3 | 10.9 |

*N.D. — not detectable

The mean plasma levels of both salicylic and acetylsalicylic acid found during this small study are historically compared to plasma levels of the same drugs seem with an equivalent single dose of 1300 mg of aspirin FIGS. 1 & 2. While the plasma levels of drug from the product of the present invention are low they do show a constant rate of release into the blood stream.

Calculation by regression analysis shows the following r values for both salicylic acid and acetylsalicylic measured after regular aspirin and aspirin formulation by the present invention as noted by Example 1 and displayed graphically in FIGS. 1 and 2.

| Regular Aspirin | Present Formulation |
|---|---|
| Salicylic Acid r = 0.126 (to 12 hours) | Salicylic Acid r = 0.941 (to 12 hours) |
| Acetylsalicylic Acid r = −0.907 (to 12 hours) | Acetylsalicylic Acid r = −0.694 (to 12 hours) |

There is no correlation with constant order release for salicylic acid in the regular aspirin, while there is a strong correlation for the plasma salicylic acid produced from the tablets of the present formulation. The negative sign (−) before the acetylsalicylic acid values indicates the degree of loss of the product from the plasma. This is important because the acetylated form of salicylic acid is approximately 50 times more potent than regular salicylic acid, in suppressing inflammation and relieving pain. As one can see from either the r values or the graphic display in FIG. 2, the formulation of the present invention produces a more steady release of acetylsalicylic acid into the blood stream whereas regular aspirin produces a rapid and high level of drug but the duration of bioavailability is limited to approximately 4 hours. This is thought to account for the fact that the regular aspirin must be taken every 4 hours to be therapeutically effective.

EXAMPLES 8–11

The following clinical cases demonstrate the prolonged therapeutic effect of the present formulation as well as the lower incidence of side effects of the present formulation. Tablets containing 650 mg of aspirin were made according to Example 1 and used in the following clinical studies.

Case 1: M.N.

This patient is a 42 year old white female who had a history of degenerative osteoarthritis and bursitis in the left shoulder. Before taking the tablets from the present formulation she had been taking 10–14 tablets per day of an aspirin-anti-acid drug (325 mg/tablet). Her total daily dosage of aspirin in this form averaged 4.0 grams per day. She complained of epigastric pain, nausea and buzzing in the ears. However, the drug was effective in controlling her pain.

In this study, she was given 650 mg aspirin tablets formulated as described in Example 1. The initial dose was 1300 mg twice daily. The patient noted immediate relief within 30 minutes after taking her first dose. She continued taking the drug for 3 months, varying the dosage between 2600 mg–4000 mg per day depending upon the severity of the pain. Importantly, she did not experience gastrointestinal, central nervous system or systemic signs of aspirin intolerance. She took the medication throughout this period on a twice daily dosage.

Case 2: M.R.

This patient is a 53 year old nurse who had documented degenrative arthritis. She had been treated with a nonsteroidal anti-inflammatory drug, CLINORIL ®, 150 mg twice daily. The drug was effective in relieving the arthritic pain but was causing her to have epigastric pain and headaches.

The patient was given aspirin formulated according to Example 1 and containing 650 mg per tablet. The initial dose was 1300 mg (two tablets) twice daily. Within 2 days of stopping the Clinoril ® and starting on the aspirin formulation herein described, the patient experienced total pain relief for 24 hours. She particularly noted the absence of abdominal pain and heartburn. This lady was successfully treated with the formulation of this invention for 3 months. During that time her average daily dosage of drug varied between 1300 mg (one tablet twice daily) to 3250 mg (three tablets at bedtime and two in the morning.) On questioning, she denied any aspirin-like side effects and stated that "this drug is as good as the other one I was taking except it doesn't bother my stomach." She however could not differentiate any significant differences in pain relief between the drug formulation of this application and Clinoril ®.

Case 3: G.G.

This case is a 44 year old white male who had acute tendinitis and bursitis of his right elbow and shoulder. He had previously used a non-aspirin (acetaminophen) proprietary drug product, because aspirin caused him to have hearburn and abdominal pain. The acetaminophen drugs were not particularly effective in relieving the tenderness and pain.

The patient took 1950 mg (3–650 mg aspirin tablets) made by the present invention twice daily for 7 days. Within 24 hours most of the pain was abolished and the tenderness subsided within 48–56 hours. There was no complaint of epigastric pain, nausea, heartburn or ringing in the ears.

Case 4: S.L.

A 26 year old white nurse was not taking any form of medication and complained of painful menstrual cramps. She requested that she be given the aspirin tablets made as in Example 1 to determine if this might have any beneficial effect on her cyclic menstrual pain.

During the first day of her menses, cramps developed and she took 1300 mg of constant order release aspirin as described. Within 45 minutes after ingestion the cramps were abolished and did not recur until 14 hours later. This finding is important since menstrual cramps are mediated in part by prostaglandins and acetylsalicylic acid is an in vivo inhibitor of prostaglandin synthesis. By reason of deduction one may conjecture that the low but constant release of acetylsalicylic and salicylic acid are effective inhibitors of prostaglandin mediate uterine cramps.

I claim:

1. A constant order release aspirin tablet comprising aspirin, from 0.5 to 10 weight percent of a hydrogenated vegetable oil, from 0.5 to 7.0 weight percent of a saccharide selected from the group consisting of lactose, sucrose, dextrose, fructose and maltose, and a lubricant.

2. The aspirin tablet of claim 1 wherein said hydrogenated vegetable oil is hydrogenated cotton seed oil.

3. The aspirin tablet of claim 2 wherein said aspirin tablet includes from 1 to 6 weight percent of hydrogenated cottonseed oil.

4. The aspirin tablet of claim 1 wherein said tablet additionally comprises from 0.15 to 1.5 weight percent of a cellulose ether, cellulose ester or a combination thereof.

5. The aspirin tablet of claim 1, 2, 3 or 4 wherein said saccharide is lactose.

6. A constant order release aspirin tablet comprising aspirin, from 0.5 to 10 weight percent of hydrogenated cottonseed oil, from 0.5 to 7.0 weight percent of lactose and a lubricant.

7. A constant order release aspirin tablet comprising aspirin, from 0.5 to 10 weight percent of hydrogenated cottonseed oil, from 0.5 to 7.0 weight percent of lactose, from 0.15 to 1.5 weight percent of a cellulose ether, cellulose ester or a combination thereof, and a lubricant.

8. A method of producing a control release aspirin tablet comprising the steps of dissolving from 0.5 to 10 weight percent of a hydrogenated vegetable oil in a suitable solvent, admixing said solution with a dry-blended mixture of from 85 to 98 weight percent of aspirin and from 0.5 to 7.0 weight percent of a saccharide selected from the group consisting of lactose, sucrose, dextrose, fructose and maltose to form a wet granulation, drying said wet granulation, sizing said granules, blending said sized granules with a lubricant and thereafter compressing said dried, sized granules into tablets.

9. The method of claim 8 wherein from 0.15 to 1.5 weight percent of a cellulose ether, cellulose ester or a combination thereof is added to said solvent.

10. The method of claim 8 or 9 wherein said hydrogenated vegetable oil is hydrogenated cottonseed oil.

11. The method of claim 8, 9 or 10 wherein said solvent is a mixture of methylene chloride and denatured alcohol.

12. The method of claim 11 wherein said solvent mixture is a 1:1 mixture.

13. The method of claim 8, 9 or 10 wherein said saccharide is lactose.

* * * * *